(12) United States Patent
Hart et al.

(10) Patent No.: US 6,258,105 B1
(45) Date of Patent: Jul. 10, 2001

(54) MALLEABLE CLIP APPLIER AND METHOD

(76) Inventors: Charles C. Hart, 8252 Mandeville, Huntington Beach, CA (US) 92646; Donald L. Gadberry, 33862 Mariana Dr., Apartment B, Dana Point, CA (US) 92629

( * ) Notice: Subject to any disclaimer, the term of this patent is extended or adjusted under 35 U.S.C. 154(b) by 0 days.

(21) Appl. No.: 09/171,287
(22) PCT Filed: Apr. 17, 1997
(86) PCT No.: PCT/US97/06586
§ 371 Date: Oct. 15, 1998
§ 102(e) Date: Oct. 15, 1998
(87) PCT Pub. No.: WO97/38634
PCT Pub. Date: Oct. 23, 1997

Related U.S. Application Data

(60) Provisional application No. 60/015,578, filed on Apr. 18, 1996.

(51) Int. Cl.[7] .................................................. A61B 17/10
(52) U.S. Cl. ............................ 606/142; 606/143; 606/158
(58) Field of Search ................................... 606/142, 143, 606/144, 139, 153; 227/901

(56) References Cited

U.S. PATENT DOCUMENTS

| 4,038,987 | * | 8/1977 | Komiya | 128/321 |
|---|---|---|---|---|
| 4,394,864 | * | 7/1983 | Sandhaus | 128/321 |
| 5,171,249 | | 12/1992 | Stefanchik et al. | 606/142 |
| 5,514,149 | | 5/1996 | Green et al. | 606/158 |

FOREIGN PATENT DOCUMENTS

WO 97/38634   10/1997   (WO) ............................ A61B/17/10

* cited by examiner

*Primary Examiner*—Henry J. Recla
*Assistant Examiner*—Lien Ngo

(57) ABSTRACT

An endoscopic clip applier for the temporary as well as permanent occlusion of vessels and the clipping of other tissues. The clip applier includes an elongated outer body having a proximal end attached to an actuating mechanism and a distal end. An elongated inner member is slidably positioned within the outer body and has a proximal end coupled to the actuating mechanism and a distal end coupled to a pair of generally opposing jaws. Movement of the inner member relative to the outer body pivots the jaws open and closed. The jaws are configured for receiving and supporting a malleable surgical clip which is insertable within an internal retention groove within each jaw. Each groove has an undercut portion at its distal end which is configured to mate with an outwardly tapering portion at the distal end of each clip. When forced distally in the grooves, the distal ends of the clip are moved into the undercut portion and the clip retained within the groove. The clip may then be compressed and opened any number of times to facilitate its insertion, placement and removal.

23 Claims, 3 Drawing Sheets

FIG. 8a
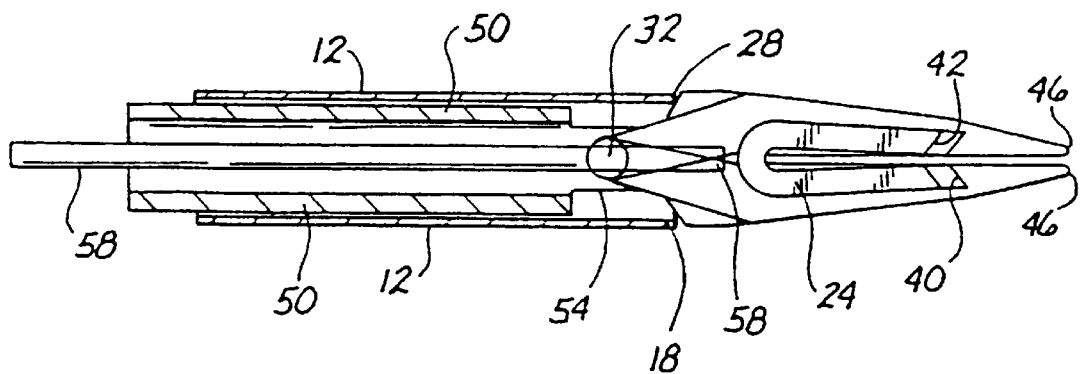
FIG. 8b
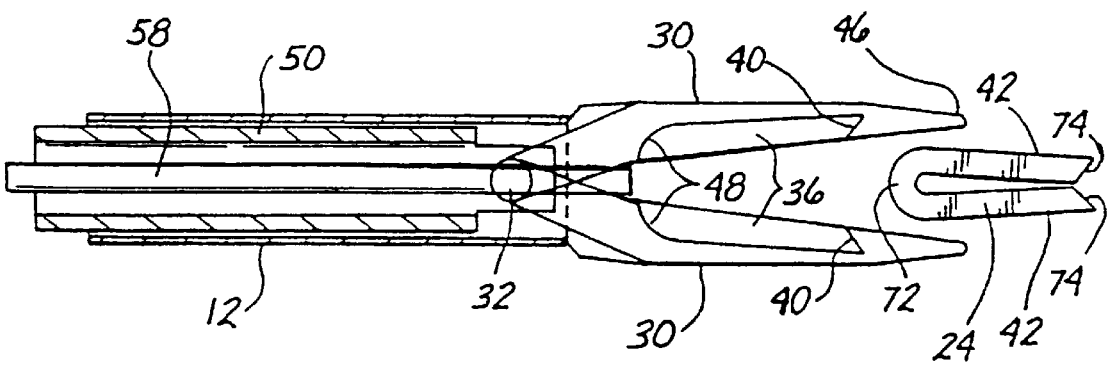
FIG. 8c

MALLEABLE CLIP APPLIER AND METHOD

RELATED APPLICATIONS

This application claims the benefit of U.S. Provisional Application No. 60/015,578, filed Apr. 18, 1996.

FIELD OF THE INVENTION

This invention relates generally to surgical clip appliers and surgical clips and, more particularly, to and endoscopic surgical clip applier for use with malleable surgical clips.

BACKGROUND OF THE INVENTION

Endoscopic surgical techniques, including laparoscopic and arthroscopic techniques, are gaining wide acceptance and are being increasingly used. There are many benefits associated with these minimally invasive techniques, including reduced patient trauma, reduced risk of post-operative infection and a reduced recovery time.

Various types of surgical instruments have been developed for use with these endoscopic surgical techniques and procedures, including clip appliers for the occlusion and ligation of vessels or other conduits and tissues. Conventional clip appliers, as currently used in these endoscopic procedures, typically consist of a frame connected to an actuating mechanism. A pair of clip compressing devices or jaws are supported at the distal end of the frame. The jaws typically consist of a pair of opposing jaw members which are movable with respect to each other. Each of the jaw members may include a slot or other means for retaining each of the legs of a surgical ligating clip. The outer surfaces of the jaw members may include cam surfaces which allow for movement by the actuating mechanism. In this configuration, the jaws are actuated by sliding an outer frame member over the cam surfaces, thereby forcing the jaw members towards each other. The ligating clips are insertable between the jaw members and within the inner grooves.

A conventional ligating clip has a pair of outwardly extending legs connected at an apex. The legs typically extend in a V-shaped or U-shaped manner from the apex and then change directions angularly at a knee portion to extend outward from the apex.

There are several deficiencies associated with the conventional endoscopic ligating clip appliers as described and as currently used. For instance, when using a ligating clip applier in an endoscopic procedure, the instrument is initially inserted through a cannula of an endoscopic trocar so that the clip may be positioned on the vessel or other tissue. The size of the vessel or tissue to be ligated is limited by the size of the clip being applied. In general, a larger vessel or tissue requires a larger clip. However, the size of the ligating clip is limited, in part, by the internal diameter of the trocar through which the ligating clip applier must be inserted.

In one version of the conventional ligating clip applier as previously described, the clip is retained within the jaw members. The jaw members extend outwardly from the frame but the opening between the jaws remains in substantial alignment with the longitudinal axis of the clip applier. A clip is inserted into the open jaws or into the hollow frame which is then passed through a trocar and manipulated within the patient until it is positioned around the tissue to be clipped. In this configuration, the open jaw members supporting the outwardly extending legs of the clip, or alternatively, the hollow frame member holding the open clip must define a diameter smaller than the internal diameter of the cannula. Otherwise, the clip applier can not pass through the trocar cannula.

In an alternative clip applier configuration, where the jaws move in an orientation perpendicular to the longitudinal axis, the size of the clip is also limited by the inner diameter of the cannula. In this configuration, the length of the clip from the end of the legs to the apex (length) must be smaller than the inner diameter of the cannula. Therefore, the overall width and length of the clip are limiting factors with regard to insertion through a trocar.

Another deficiency associated with conventional ligating clip appliers is the difficulty the endoscopic surgeon encounters when attempting to control the position of the clip during application. Often times, a clip is either improperly applied or applied to the wrong location. In these instances, the surgeon is required to apply another clip to the appropriate location. In addition, the surgeon must now remove or leave in the patient, at least two clips. Thus, there is a need for an endoscopic clip applier and associated ligating clip which may be repositioned during surgery and is also easily removed from the applied tissue.

Yet another deficiency associated with conventional ligating clip appliers and ligating clips is that the legs of the clip typically protrude inwardly from the inner jaw surfaces of the clip applier. This makes manipulation of the clip applier and clip within the patient more difficult. In part, this is due to the configuration of the jaws of a conventional ligating clip applier, wherein the jaw members do not wholly retain the legs of the clip within their inner surfaces. In other clip applier configurations, the deficiency is due in part to the configuration of the clip which has legs protruding outwardly from the distal ends of the jaws.

What is needed in this field, is an endoscopic clip applier and associated clip which overcomes these deficiencies and which is easy to use by the endoscopic surgeon and is economical to manufacture.

SUMMARY OF THE INVENTION

The present invention satisfies the need for clip applier for ligating and occluding vessels and other tissues by providing an endoscopic clip applier that is capable of inserting a surgical clip through a cannula while being maintained in a minimum diameter configuration. By inserting the surgical clip into the opposing jaw members of the clip applier and then closing the jaws such that the width (diameter) of the clip is minimized, a clip of almost any size may be passed through a conventional cannula. This allows the ligating and occluding of almost any size vessel or other tissue while using conventional endoscopic techniques. For purposes of this disclosure, endoscopic is defined to include laparoscopic, arthroscopic as well as any other surgical techniques related to the use of a trocar or small entry incision.

The present invention also satisfies the need for a clip applier and associated surgical clip that is easy to manipulate within a patient and minimizes contact and damage to surrounding tissues. This is accomplished by fully retaining the clip within the jaw members such that there are little or no protruding portions. In addition, the jaw members of the present endoscopic clip applier protrude beyond the surgical clip, providing a smooth continuous surface for ease of manipulation within a patient.

The present invention also satisfies the need for a clip applier for occluding and ligating vessels and other tissues which is capable of both repositioning and removing a previously applied surgical clip. This is accomplished by providing a retention groove having an undercut portion within each jaw member. In operation, the jaw members are closed around the clip which is then forced or otherwise moved forwardly such that the distal portion of each clip leg is retained within the undercut portion of each retention groove. The clip is thus retained within the jaw members whether the clip is opened or compressed closed. By providing a clip made from a malleable material, the clip may be opened and closed, repositioned, reused or removed a plurality of times.

The present invention is generally directed to an improved endoscopic clip applier for applying a surgical clip having outwardly extending legs to occlude or otherwise ligate a vessel or other tissue. Broadly speaking, the clip applier of the present invention includes an elongated outer body which defines a longitudinal axis between a proximal end and a distal end. An operating assembly is supported at the distal end.

The operating assembly includes a pair of generally opposing jaw members which extend outwardly from the elongated body. Each jaw member has a retention groove which extends generally longitudinally along an inner surface and terminates into an undercut portion. The groove and undercut portion are configured for releasably retaining the surgical clip within the opposing inner surfaces of the jaw members. An actuating mechanism is attached to the proximal end of the elongated outer body. Actuation of this mechanism moves the coupled jaw members between an open position and a closed position.

In the closed position, the jaw members contact each other across their opposing inner surfaces and generally along the longitudinal axis of the clip applier. With this configuration, a surgical clip of most any size may be utilized and is generally only limited by the longitudinal length of the jaw members.

In another broad aspect of the present invention, each of the jaw members includes a generally longitudinal retention groove or groove which is sufficiently long and sufficiently deep such that a substantial portion of the clip is retained flush relative to the inner surface of the jaw member. In this way, the clip may be retained within the jaw members without protruding from the jaw's inner surface. This configuration allows the jaw members to fully close along their inner surfaces as well as providing a smooth and continuous inner surface when the jaws are open.

In yet another broad aspect of the present invention, the surgical clip is made from a malleable material such that the clip may be inserted into the endoscopic clip applier and closed and opened a plurality of times. In this way, a clip may be inserted into the clip applier, applied to a vessel or other tissue within the patient, repositioned a plurality of times and later removed. The clip is a generally U-shaped or V-shaped clip which has a pair of outwardly extending and generally opposed legs. An intermediate portion connects the legs at their proximal ends to form an apex.

In yet another broad aspect of the present invention, the undercut portion of each jaw member is sized and configured to allow the distal ends of an associated surgical clip to fit inside or underneath. In this way, each leg of the clip is positively retained within each jaw member. More specifically, each undercut portion defines an inwardly tapering portion or overhang at the distal end of each groove. In a similar and compatible fashion, the distal end of each clip terminates in an outwardly tapering portion or tab which fits against the inwardly tapering undercut portion of each jaw member. Thus when the clip is pushed or otherwise moved forwardly within the grooves, the outwardly tapering portion of each leg fits within the inwardly tapering portion of the undercut portion and is thus physically retained within the jaw members.

In another embodiment of the present invention, the endoscopic clip applier includes a hollow elongated outer body which has a proximal end connected to an actuating mechanism and a distal end. An elongated inner member is also attached to the actuating mechanism at its proximal end and extends distally in a coaxial fashion with the elongated outer body. This inner member is movable relative to the outer body by operation of the actuating mechanism. An operating assembly is coupled to the distal end of the inner member. The operating assembly includes a pair of pivotally opposing jaw members as previously described.

A push member or retention shaft is also coupled to the actuating mechanism. The push member is configured for contacting and applying a force against a proximal end (apex) of the clip such that the clip is moved forwardly or distally within the grooves. In this fashion, the distally tapered portion of each leg is forced into the undercut portion of each jaw member. The actuating mechanism is configured to remotely move at least one of the jaw members between a closed position and an open position.

The actuating mechanism includes a main body which is connected to the proximal end of the outer body and an actuating handle which is coupled to the main body and connected to the proximal end of the inner member. In this way, movement of the handle in relation to the main body forces the jaw members to move distally and proximally relative to the fixed outer body. A cammed surface or taper on the outer surface of each jaw member in contact with the distal end of the outer body causes the jaws to move relative to each other as the inner member and outer body are moved. A biasing spring is included for forcing the handle in one direction with respect to the main body such that the jaw members are normally maintained in the closed position. A second handle or actuating mechanism is coupled to the main body for actuating the push member. A second biasing spring is coupled to the actuating mechanism for forcibly maintaining the push member against the clip.

A method of applying a surgical clip to a vessel or other tissue in a patient according to the principals of the present invention includes the steps of placing a malleable surgical clip which has a pair of outwardly extending legs within the jaw members of a clip applier as presently disclosed such that each leg is retained within the undercut portion of each groove. The jaw members are then closed such that the retained legs of the clip are compressed together and the width and diameter of the clip is minimized. The clip applier is then inserted and positioned within the patient such that the closed jaw members are placed adjacent the vessel or other tissue to be clipped. The jaw members along with the retained clip, are then opened. The open jaw members are manipulated or positioned within the patient such that the legs of the retained clip extend over the tissue. The jaw members are then closed such that the legs of the clip are compressed over the vessel or other tissue. The clip applier is then removed from the patient.

In another broad aspect of the present invention, the method includes the step of applying a distal or forward force on the clip while within the jaw members such that the distal portions of each leg are forced into the undercut portions of each jaw member. This step retains the clip within the jaw members.

In yet another broad aspect of the invention, the surgical clip is removed from within the jaw members by relieving the distal or forward force on the proximal end of the clip. The jaw members are then slightly opened to relieve any compressive pressure on the clips by the closed jaw members. This action allows the clip to move freely within the grooves. The clip applier is then moved distally or forward relative to the clip such that the distal portions of the legs are withdrawn from within the undercut portions of each jaw member. The jaw members are then opened such that the clip is left compressed on the tissue. The clip applier is then removed from the patient.

The invention, together with the additional features and advantages thereof, which was only summarized in the foregoing passages, will become more apparent to those of skill in the art upon reading the description of the preferred embodiments, which follows in the specification, taken together with the following drawings.

BRIEF DESCRIPTION OF THE DRAWINGS

FIG. 8a is a sectional view of the clip applier as depicted in FIG. 1, shown having a retracted push member;

FIG. 8b illustrates the clip applier as depicted in FIG. 2, shown with the push member withdrawn and the jaw members partially opened; and FIG. 8c illustrates the clip applier as depicted in FIG. 8b, shown with the jaws partially opened and the clip applier withdrawn.

DESCRIPTION OF THE PREFERRED EMBODIMENTS

Figure 1:
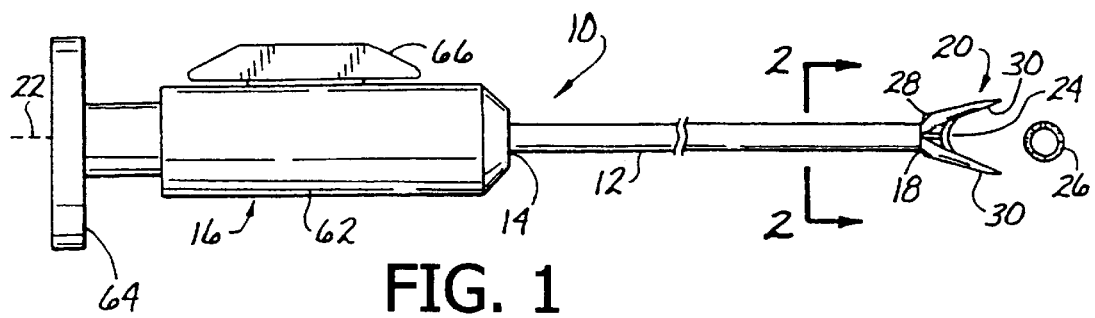
FIG. 1 is a side elevational view of an embodiment of an endoscopic clip applier according to the principles of the present invention, the applier shown adjacent a vessel to be occluded.

Referring now to the drawings, wherein like reference characters designate identical or corresponding parts throughout the several views, an endoscopic clip applier of the present invention is illustrated in FIG. 1 and generally indicated by reference numeral 10.

As shown, the clip applier 10 of the present invention includes an elongated outer body 12 having a proximal end 14 connected to an actuating mechanism 16 and a distal end 18 coupled to an operating assembly 20. A longitudinal axis 22 is generally defined along the elongated body 12. A surgical clip 24 is insertable within the operating assembly 20 for occluding a vessel 26 or for ligating other tissue.

The elongated body 12 which may be an elongated rigid shaft having distal end 18 and proximal end 14 and an axial passage 22 therebetween. The elongated body 12 may be made from a variety of rigid biocompatible materials including a metal such as stainless steel, a plastic such as acrylonitrile-butadiene-styrene (ABS), a polycarbonate material or the like. In a preferred embodiment, the elongated body 12 is rigid, however it may also be made from a compliant material to allow some flexibility in the shaft.

In a preferred embodiment, the elongated body 12 may comprise a relatively narrow outer diameter facilitating insertion into and through a trocar, a cannula or a small incision. The tubular structure 12 preferably includes a wall having sufficient thickness to structurally support the operating assembly 20, its operation and any required manipulation within a patient. Preferably, the elongated body 12 has a rounded cross-section which may be circular or oval, for example.

The proximal end 14 of the elongated body 12 is preferably rigidly secured to the actuating mechanism 16 such that the endoscopic clip applier 10 is a generally structurally rigid device. Thus, the proximal end may be attached to the actuating mechanism 16 using any of the wide variety of methods available and known to those of skill in the art of manufacturing surgical devices. As an example, the proximal end 14 may be attached to the actuating mechanism 16 through welding, the use of adhesives, fasteners, or a threaded fitting.

The distal end 18 of the elongated body 12 is coupled to the operating assembly 20 to provide structural support as well to allow the operating assembly 20 to be moved between an open position and a closed position. In a preferred embodiment, the elongated body 12, which may be a hollow tubular member, is not directly attached to the operating assembly 20 but is operatively moved relative to a tapered or cammed outer surface 28 on opposing sides of the operating assembly 20. This movement over the cam surfaces 28 moves the operating assembly 20 between an open position and a closed position.

Referring now to FIGS. 2–5, the endoscopic clip applier 10, and more specifically the operating assembly 20, will be described in greater detail. The operating assembly 20 includes a pair of generally opposing jaw members 30. Each of the jaw members 30 extends outwardly from a pivot point 32 adjacent the distal end 18 of the elongated body 12.

Figure 2:
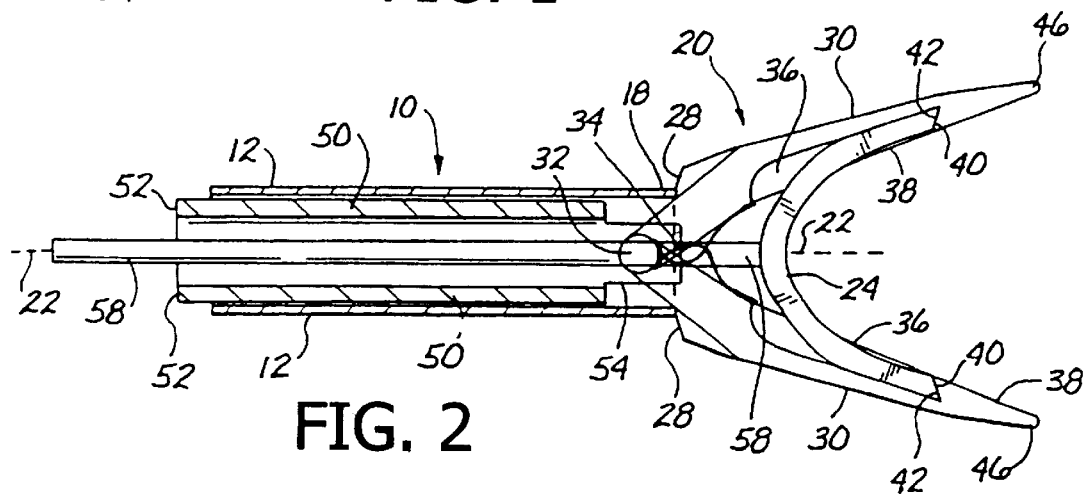
FIG. 2 is a sectional view of the clip applier as depicted in FIG. 1, taken along lines 2—2.

Alternatively, each of the jaw members 30 may extend from a separate pivot point. Another configuration contemplates one of the jaw members 30 being fixed with the other pivotable. A first biasing spring 34 as can be see in FIG. 2, may be inserted between the jaw members 30 to retain the jaw members in a normally closed position. However, the jaw members 30 may be maintained in normally closed position through use of other methods as are commonly to known to those of skill in the art of similar devices. Alternatively, the biasing spring 34 may be used to maintain the jaw members 30 in the open position as shown in FIG. 2. In yet another configuration, the operating assembly 20 may be provided without any biasing spring or other mechanism.

In the illustrated embodiment, a groove 36 extends longitudinally along an inner surface 38 of each jaw member 30. Preferably, each groove 36 extends distally from a proximal point on the inner surface 38, and terminates in an undercut portion 40. This undercut portion 40 which may also be a bore, or an overhang portion, is configured for releasably retaining the distal end of a clip leg 42 as will be further described. In addition, each jaw member 30 preferably extends distally beyond the undercut portion 40 such that the clip 20 is fully retained within the jaw members 30. Thus, the clip 20 is fully retained within the jaw members 30 when the operative assembly 20 is in the closed position. Alternatively, when the operating assembly 20 is in the open position, the clip 20 is maintained within the grooves 36 such that a smooth and generally flush surface is provided along the inner surface 38 of each jaw member 30. In this way, a surgeon may manipulate the clip applier 10 within a patient with the jaw members 30 open, without fear of catching, tearing or otherwise damaging tissue because of a protruding clip or other non-smooth surface.

Figure 6A:
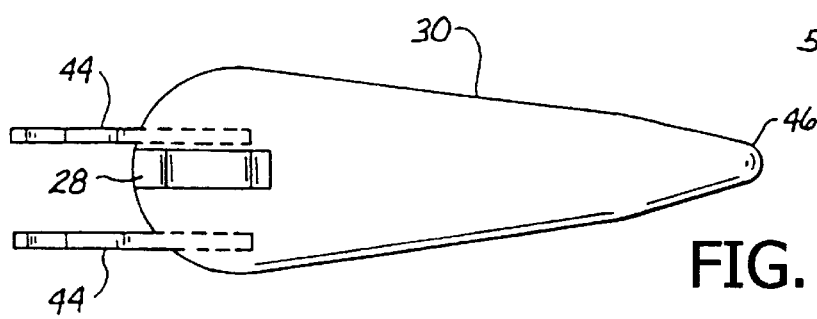
FIG. 6a is a top view of a jaw member as depicted in FIG. 1.
Figure 6B:
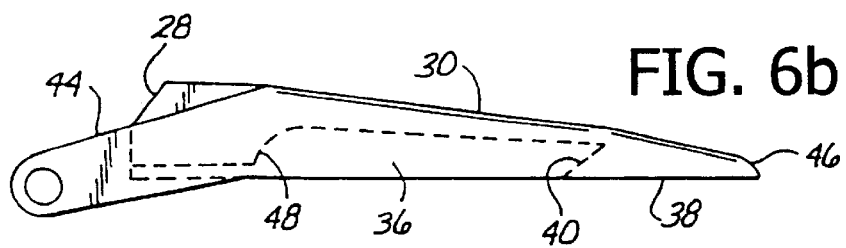
FIG. 6b is a side view of a jaw member as depicted in FIG. 1.
Figure 6C:
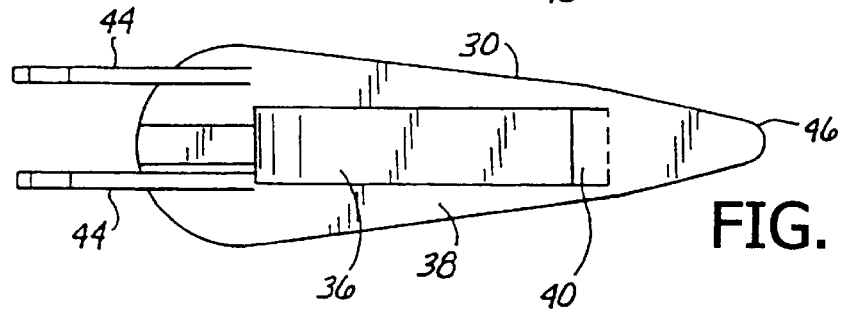
FIG. 6c is a view of the interior of a jaw member as depicted in FIG. 1.

Referring now to FIGS. 6a–6c, an embodiment of the jaw members 30 according to the present invention will generally be described. Each jaw member 30 includes a pivot clevis 44 at a proximal end and includes a bore 45 for receiving a pivoting axis or shaft. In a preferred embodiment, each jaw 30 generally tapers downwardly to a smooth rounded front distal end 46. This configuration is preferably minimized in width or diameter so it may be passed through a cannula, trocar or even a small incision in the patient.

Each jaw member 30 includes a groove 36 having a smooth proximal portion 48 and an undercut portion 40 as previously described. The smooth proximal portion 48 is preferably configured such that the surgical clip 24 may fit smoothly and flush within the groove 26. Alternatively, the smooth proximal portion 48 may be configured such that the surgical clip 24 is properly supported during compression allowing proper closure or clipping against the vessel to be occluded or other tissue. As can be seen in FIG. 6b, the undercut portion 40 may be an inward taper and preferably defines an angle of approximately 30 to 60 degrees from the inner surface 38 or longitudinal axis 22 when in the closed position. However, other angles as well as other undercut configurations may be used.

The main object of the undercut portion 40 is to releasably retain the surgical clip 24 inserted within the grooves 36, and more particularly, whose distal ends 42 are pushed inwardly against the undercut portion 40. The undercut portion 40 is also designed such that the clip 20 is easily released from the grooves 36 when the surgical clip 24 is moved proximally or rearwardly within the grooves. This movement frees the distal ends 42 from the undercut portions 40 and allows the jaw members 30 to be pivoted away leaving the clip 20 behind.

As previously mentioned, the distal ends 46 of each jaw member 30 extend distally beyond the undercut portion 40. The inner surface 38 of each jaw member 30 adjacent the clip 20 is typically flat such that the opposing jaw members 30 lay fully closed along the longitudinal axis 22. A tapered or angled surface leading distally from the pivot clevis 44 is provided along the outer proximal portion of each jaw member 30 to a cammed outer surface 28. In a preferred embodiment, each jaw member 30 is generally symmetrical with the exception of the pivot clevis 44 which are moved laterally to insure proper alignment with pivot point 32. However, jaw members 30 may be provided which are identical but do not pivot from a common point or alternatively, jaw members 30 may be provided which are asymmetrical. In another embodiment, one jaw member 30 is generally fixed while the remaining jaw member 30 pivots.

Referring now back to FIGS. 2–5, an elongated inner member 50 is provided to facilitate actuation of the operating assembly 20. The elongated inner member 50 preferably includes a proximal end 52 which is attached to the actuating mechanism 16 and a distal end 54 which is coupled to the jaw members 30 through pivot point 32. The elongated inner member 50 is preferably a shaft, sleeve or a tubular member similar to the elongated outer body 12 but of a smaller maximum diameter such that it is slidable within the elongated outer body 12 by actuation of the actuating mechanism 16.

Figure 4:
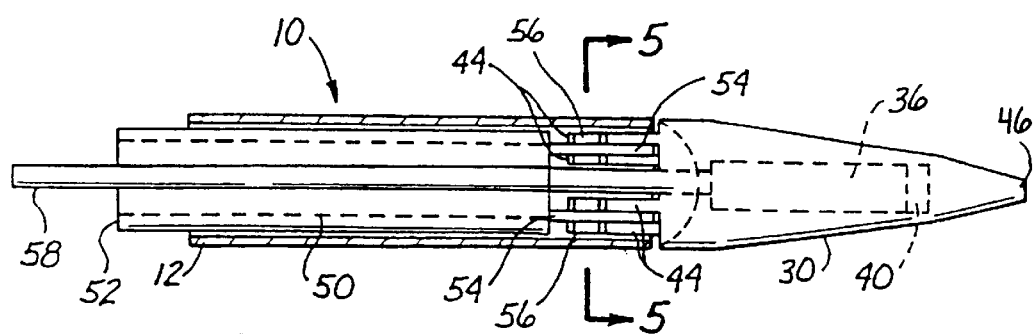
FIG. 4 illustrates the clip applier as shown in FIGS. 2 and 3, rotated 90 degrees.
Figure 5:
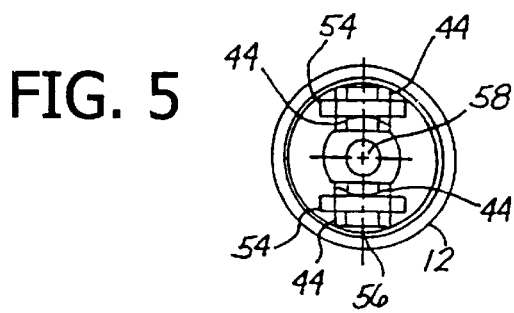
FIG. 5 is a cross-sectional view of the clip applier as depicted in FIG. 4 taken along lines 5—5.

As can be seen in FIGS. 4–5, the distal end 54 may comprise two extending members or clevis support tabs. Preferably, these distal ends 54 are configured so that each one fits between the pivot devises 44 extending from each jaw member 30. A pivot axis 56, or preferably a pair of pivot axes 56, may then be provided to retain each jaw member 30 to each of the distal ends 54 as shown in FIGS. 4 and 5.

A push member 58 may be provided within the elongated inner member 50 to provide a distal or forwardly applied force on the surgical clip 24. In this way, the push member 58 is moved distally within the elongated inner member 50 and contacts the proximal portion of the clip 24 forcing the clip 24 to move distally within the grooves 36 such that the distal end of each clip leg 42 is forced within the undercut portion 40 of each groove 36. By maintaining the distal or forwardly force on the push member 58, the surgical clip is held retained within the jaw members 30.

A biasing spring 60 may be provided to maintain a continuous forward or distal force on the push member 58 such that the surgical clip 24 is held retained within the jaw members 30. However, alternative methods of maintaining a distal or forwardly force against the surgical clip 24 may be utilized. For example, pneumatic pressure directed against the surgical clip 24, magnetic attraction of the clip into the undercut portion 40 or any other method of maintaining the surgical clip 24 within the undercut portion 40 as is contemplatable by those of skill in the art.

Figure 3:
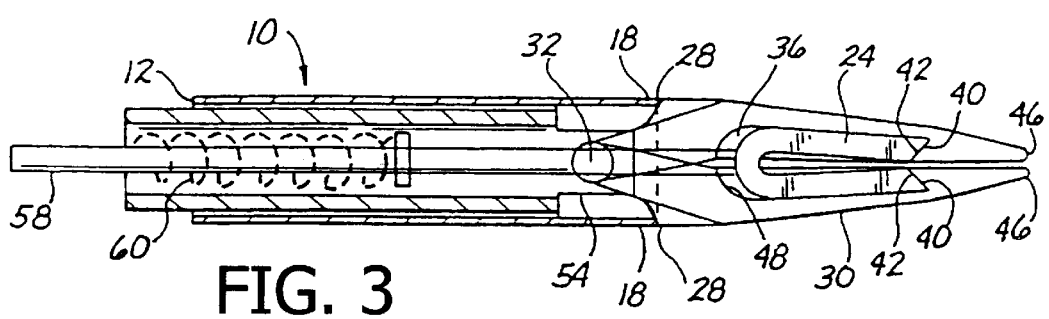
FIG. 3 illustrates the clip applier as depicted in FIG. 2 shown in the closed position.

Referring now back to FIGS. 1–3, the actuating mechanism 16 may include any device which moves the inner member 50 relative to the outer body 12. As shown in FIG. 1, the actuating mechanism 16 may include a main body 62 which is connected to the outer body 12 as previously. An actuating handle 64 may be movably coupled to the main body 62 of the elongated inner member 50. In this fashion, when the handle 64 is moved relative to the main body 62, the elongated inner member 50 is moved within and relative to the elongated outer body 12. More specifically, when the handle 64 is moved rearwardly or pulled outwardly from the main body 62, the elongated inner member 50 is retracted inwardly or proximally from the elongated outer body 12. This action draws the jaw members 30 within the distal end 18 of the elongated outer body 12.

As the jaw members 30 are drawn proximally into the generally open and hollow elongated outer body 12, the distal end 18 contacts and slides against the tapered or cammed outer surface 28 of each jaw member 30. As this tapered cammed outer surface 28 continues to be drawn inwardly into the distal end 18 of the elongated outer body 12, the jaw members 30 are forcibly closed as shown in FIG. 3.

Conversely, moving the handle 64 distally or forwardly into the main body 62 pushes the elongated inner member 50 relative the elongated outer body 12 and forces the jaw members 30 outwardly or distally from the distal end 18. As the jaw members 30 are moved distally out of the elongated outer body 12, the first biasing spring 34 forces the jaw members 30 into the open position. Alternatively, the first biasing spring 34 may be coupled with the actuating handle 64 for forcing the handle in one direction with respect to the main body 62 such that the jaw members 30 are normally maintained in either the opened or closed position. Alternatively, the first biasing spring 34 may be supplied in two configurations, the first for maintaining the handle 64 outwardly from the main body 62 such that it must be pushed by the surgeon to actuate the operating assembly 20 or alternatively where the handle 64 is maintained adjacent the main body 62 such that the surgeon must pull to actuate the operating assembly.

A second actuating handle 66 may be movably coupled to the main body 62 for actuation of the push member 58. The push member 58 may preferably be a shaft or rod extending from the second actuating handle 66 slidably through the elongated inner member 50 and between pivot axes 56, as shown in FIGS. 4 and 5, to contact the surgical clip 24. The biasing spring 60 may be then coupled anywhere within the elongated inner member 50 but is preferably coupled to the second actuating handle 66 such that the push member 58 is normally held against the surgical clip 24 and thus requires physical action by the surgeon to retract the push member 58 removing the force against the clip 24.

Figure 7:
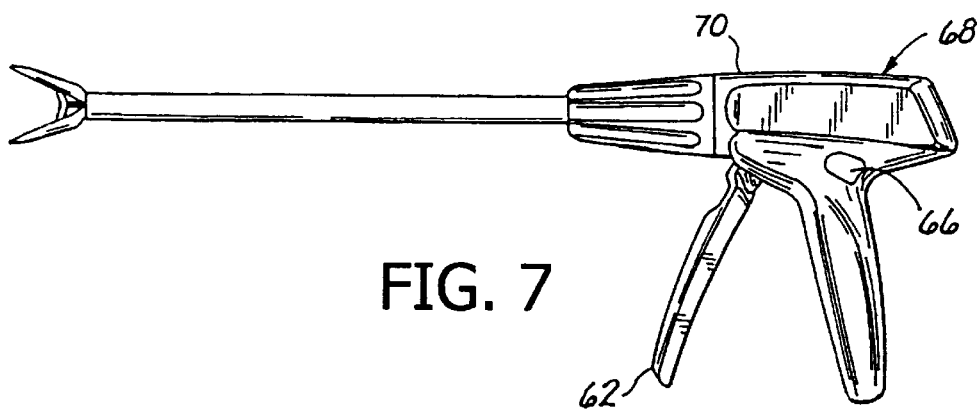
FIG. 7 is a side elevational view of an embodiment of a clip applier of the present invention, shown having an alternative actuating mechanism.

Referring now to FIG. 7, an alternative actuating mechanism 68 is shown. In this configuration, the main body 70 is similar to that previously described. However, the actuating handle 62 may be styled as a hand grip. A biasing spring (not known) may be used to maintain the actuating handle 62 in the outward position such that the surgeon must compress it to either close or open the operating assembly 20. Preferably, movement of the actuating handle 62 opens or closes the operating assembly 20 without effect on the push member 58 which is maintained forcibly against the clip 24. In this configuration, the surgeon or other operator must actively remove or otherwise retract the push member 58 from against the clip 24.

In yet another configuration, the elongated inner member 50 may be fixedly attached to the main body 70 and the elongated outer body 12 movably attached to the actuating handle 62. In this fashion, movement of the actuating handle 62 may provide a closing and opening effect on a modified operating assembly. In this configuration, a single fixed jaw and a pivoting jaw may be preferred. However, alternative mechanisms may be included within the main body to achieve differing actions and compressive strengths on the jaw members 30. Alternatively, other methods may be used to open and close the jaw assemblies as well as for actuating mechanisms as is commonly known or contemplated to those of skill in the art.

The surgical clip 24 is preferably a U-shaped or V-shaped surgical clip which has a pair of generally opposed legs 42. An intermediate portion 74 interconnects the respective legs 42. This U-shaped clip 24 is meant to include V or other similarly shaped clips. Preferably, the clip 24 is made from a malleable material which allows it to be compressed or closed within the jaw members 30 and then reopened several times. Thus, the material may include any biocompatible material which is flexible yet maintains sufficient strength such that it may occlude or otherwise clip tissue. Such a clip 24 may be made from titanium, alloys of titanium, or a stainless steel.

As previously described, the distal end of each clip leg 42 preferably terminates in an outward taper 76 or similar such that it is retainable within the undercut portion 40 within each jaw member 30. Preferably, this outward taper defines an angle of approximately 30 to 60 degrees from the clip leg 42 and preferably matches the angle of the undercut portion 40.

The clip legs 42 preferably have a cross-sectional size or area that fits within each groove 36 such that the inner surface 38 of each jaw member 30 is a smooth continuous surface even with the clip 24 inserted. It is an important feature of the present invention that the clip 24 fits within the grooves 36 and that the distal ends of the legs 42 are slidable such that they are retained within the undercut portions 40, regardless of the clips 24 shape or cross-section and regardless of the shape of the undercut portion 40.

Referring now to FIGS. 2, 3, and 8a–8c, a method of using an endoscopic clip applier 10 of the present invention in an endoscopic surgical procedure (which includes laparoscopic as well as arthroscopic procedures for purposes of this disclosure) will be described. Initially a malleable clip is loaded or otherwise inserted between jaw members 30 by inserting the clip legs 42 into the grooves 36. The push member 58 may be then used to slidably force the clip 24 forwardly or distally within the grooves 36 such that the outward taper 76 on the distal end of each clip leg 42 is moved within the undercut portion 40 of each groove 36. The jaw members 30 are then closed such that retained legs 42 of the clip 24 are compressed together. In this configuration, the diameter or overall cross-sectional area of the endoscopic clip applier 10 is minimized. This allows insertion into a cannula (not shown) of minimal diameter while supplying a surgical clip 24 of almost any size.

The clip applier 10 is then manipulated within the patient such that the closed jaw members 30 are moved adjacent to a vessel or tissue to be clipped. The jaw members 30 are then opened using the actuating mechanism 16 and the clip applier 10 moved forwardly or otherwise manipulated within the patient such that the clip 24 extends over and generally surrounds the vessel or tissue. The actuating mechanism can then be actuated again such that the jaw members 30 are closed and the clip legs 42 compressed over the vessel and tissue, thus occluding or clipping the tissue.

The actuating mechanism 16 may again be actuated to pivot the jaw members 30 for relieving any compressive pressure on the clip 24 by the closed jaw members 30. This allows the clip 24 to now slide freely within the grooves 36. The push member 58 is then retracted or otherwise moved proximally such that the forward or distal force against the clip is removed. The clip applier 10 is then moved or manipulated within the patient such that the clip 24 is moved proximally within the groove 36. This movement, removes or withdraws the outward taper 76 on each clip leg 42 out from the undercut portion 40 of each groove 36 as shown in FIG. 7a. The actuating mechanism may then be moved such that the, jaw members 30 are opened, leaving the clip 24 remaining compressed against the vessel or other tissue.

The jaw members 30 may be partially opened as shown in FIG. 8b just sufficiently to allow retraction of the endoscopic clip applier 10 from over the vessel or other tissue and applied clip. In this fashion, any additional damage to surrounding tissue by the opened jaw member 30 can be minimized. Once the clip applier 10 has been retracted proximally of the applied clip 24, the jaw members 30 may again be closed to minimize the diameter or otherwise cross-sectional area of the clip applier 10. The clip applier 10 may then be removed from the patient.

A major advantage of the present invention is that it allows for the repositioning of a clip 24 in the event it was improperly applied. In addition, the clip applier 10 of the present invention allows for the repositioning of a previously applied clip 24 as well as for clip 24 removal. These procedures, follow the procedure previously discussed for applying a clip 24, but in a slightly different order.

To engage a clip 24, the clip applier 10 is generally inserted through a cannula or other opening into a patient while the operating assembly 20 is maintained in the minimized or closed position. The clip applier 10 is then positioned adjacent the clip 24 to be repositioned or removed. The jaw members 30 are then pivoted open sufficiently to be moved around the clip 24. Once the jaw members 30 surround the clip 24, the jaws may be pivoted closed such that they capture the clip 24. Some manipulation may be required to insure that the clip fits into the grooves 36, however the surgeon will know when the clip 24 is captured since the jaw members 30 will fully close. The push member 58 is then extended or moved distally such that a forward or distally applied force is placed on the clip 24, moving the clip 24 distally within the grooves 36 and forcing the outward taper 76 on the clip legs 42 within the undercut portion 40 of each groove 36. The clip applier 10 and the retained clip 24 may then be removed as previously described for the clip applier 10.

It will be understood that various modifications can be made to the various embodiments of the present invention herein disclosed without departing from the spirit and scope thereof. For example, various sizes of the clip applier and clip are contemplated as well as various types of construction materials. Also, various modifications may be made in the configuration of the parts and their interaction. Therefore, the above description should not be construed as limiting the invention, but merely as an exemplification of preferred embodiments thereof. Those skilled in the art will envision other modifications within the scope and spirit of the present invention as defined by the claims appended hereto.

What is claimed is:

1. An endoscopic clip applier, comprising:
   an elongated body having a proximal end and a distal end, and defining a longitudinal axis;
   an operating assembly coupled to the distal end, said assembly including a pair of pivotally opposing jaw members extending outwardly from the elongated body, each jaw member having a groove extending longitudinally along an inner surface and terminating at an overhang which defines with the groove an undercut space for releasably retaining the surgical clip within the jaw members;
   a surgical clip having legs with distal ends retained by the overhang in the undercut space of the jaw members; and
   an actuating mechanism attached to the proximal end of said elongated body of actuating the pivotally coupled jaw members and retained clip legs between an open position and a closed position.

2. An endoscopic clip applier as recited in claim 1 wherein each of the jaw members has an inner surface and said inner surfaces contact each other along the longitudinal axis when the jaw members are closed.

3. The endoscopic clip applier as recited in claim 1 wherein the clip is made from a malleable material.

4. The endoscopic clip applier as recited in claim 3 wherein said clip has a generally U-shaped configuration with a pair of generally opposed legs connected by an intermediate portion.

5. An endoscopic clip applier as recited in claim 4 wherein each of said grooves is sufficiently long and sufficiently deep that a substantial portion of the associated leg of the clip is retained flush relative to said inner surface of the associated jaw.

6. The endoscopic clip applier as recited in claim 4. wherein:
   each of the legs extends to a distal end; and
   the distal end of each leg is configured to fit within the space portion of the associated jaw member.

7. The endoscopic clip applier as recited in claim 6 wherein each overhang defines an inwardly tapering portion of each groove.

8. The endoscopic clip applier as recited in claim 7 wherein each leg of the clip terminates in an outward taper which mates with the inwardly tapered portion of each jaw member when the clip is moved distally within the grooves.

9. An endoscopic clip applier for applying a surgical clip having legs with distal ends, to a vessel or other tissue, said applier comprising:
   a hollow elongated outer body having a proximal end connected to an actuating mechanism and a distal end;
   an actuating mechanism coupled to the proximal end of the outer body;
   an elongated inner member having a proximal end and a distal end, the proximal end being attached to the actuating mechanism, said inner member extending outwardly through the elongated outer body and being slidable within the outer body by operation of the actuating mechanism;
   an operating assembly coupled to the distal end of the inner member said assembly including a pair of pivotally opposing jaw members, each jaw member having portions defining a groove extending along an inner surface, and an overhang defining with the groove portions an undercut space; and
   a push member coupled to said actuating mechanism for applying a force against the clip such that the clip is moved distally within the grooves and the distal portion of each leg is forced into the undercut space of the associated jaw member.

10. The endoscopic clip applier as recited in claim 9 wherein said actuating mechanism comprises:
    a main body connected to the proximal end of the outer body; and
    an actuating handle coupled to the main body and connected to the proximal end of the inner member such that movement of the handle in relation to the main body forces the jaw members to pivot relative to each other between an open position and a closed position.

11. The endoscopic clip applier as recited in claim 10 and further comprising a biasing spring for forcing the handle in one direction with respect to said main body such that the jaw members are normally maintained in the open position.

12. The endoscopic clip applier as recited in claim 10 wherein said actuating mechanism further comprises a stationary handle having a fixed relationship to the main body.

13. The endoscopic clip applier as recited in claim 10 wherein the push member comprises a shaft having a proximal end coupled to the actuating mechanism, the shaft extending slidably through said inner member into a contacting relationship with the clip.

14. The endoscopic clip applier as recited in claim 13 wherein the actuating mechanism comprises a biasing spring for maintaining said push member against the clip.

15. A method of applying a surgical clip to a vessel or other tissue in a patient using a clip applier having an elongated body with a proximal end attached to an actuating mechanism and a distal end coupled to a pair of pivotally opposing jaw members, each jaw member having a longitudinally extending groove terminating at an overhang which defines with the groove an undercut space for releasably retaining the surgical clip, said method comprising the steps of:

providing a malleable surgical clip having a pair of outwardly extending legs;

placing the malleable surgical clip within the jaw members such that each leg of the clip is retained in the undercut space of the associated groove;

closing the jaw members such that the retained legs of the clip are compressed together;

positioning the clip applier within the patient such that the closed jaw members are adjacent the tissue to be clipped;

opening the jaw members to force the retained legs of the clip to an open state;

positioning the jaw members and the legs of the retained clip over the tissue closing the jaw members to force the legs of the clip to a closed state over the tissue, and removing the clip applier from the patient.

16. The method of applying a surgical clip as recited in claim 15 and further comprising the step of inserting the clip applier through a surgical incision in the patient.

17. The method of applying a surgical clip as recited in claim 15 wherein the step of opening the jaw members and the step of closing the jaw members each comprises the step of actuating the actuating mechanism such that at least one jaw member is pivoted relative to the other jaw member.

18. The method of applying a surgical clip as recited in claim 15, further comprising the step of applying a distal force to the clip to move the distal portions of each leg into the undercut space of the associated jaw member.

19. The method of applying a surgical clip as recited in claim 18 wherein the step of removing the clip applier comprises the step of:

relieving the distal force on the clip; and pivoting the jaw members to relieve any compressive pressure on the clip;

withdrawing the legs of the clip from the undercut space of the associated jaw members;

opening the jaw members such that the clip is left with the tissue; and removing the clip applier from the patient.

20. The method of applying a surgical clip as recited in claim 15 and further comprising the steps of:

reinserting the clip applier into the patient such that the jaw members are positioned adjacent the clip applied to the tissue;

opening the jaw members;

positioning the jaw members over the legs of the clip;

closing the jaw members such that the jaw members surround the clip and the legs are moved into the undercut space of the associated jaw member;

opening the jaw members to remove the retained clip from the tissue; and removing the clip applier with the retained clip from the patient.

21. The method of applying a surgical clip as recited in claim 20, wherein the step of removing the clip applier comprises the steps of:

moving the clip applier proximally away from the tissue;

closing the jaw members to close the retained clip; and withdrawing the clip applier and the closed retained clip from the patient.

22. A method for repositioning a surgical clip having a pair of outwardly extending legs previously compressed over a vessel or other tissue in a patient, using a clip applier including an elongated body having a proximal end connected to an actuating mechanism and a distal end coupled to a pair of pivotally opposing jaw members, each jaw having a longitudinally extending groove terminating at an overhang which defines with the groove an undercut space, said method comprising the steps of:

positioning the jaw members within the patient with the jaw members in an open state and disposed relative to the surgical clip;

closing the jaw members to engage the clip with the legs of the clip retained in the grooves;

moving the clip longitudinally within the grooves of the jaw members to force the legs of the clip into the undercut spaces of the jaw members;

opening the jaw members to force the retained clip to an opened state;

moving the clip applier within the patient to reposition the jaw members relative to the vessel;

closing the jaw members to force the retained clip to a closed state on the vessel; and removing the clip applier from the patient.

23. The method of repositioning a surgical clip as recited in claim 21 wherein the step of moving the clip comprises forcing the clip distally within the grooves.

\* \* \* \* \*